United States Patent [19]

Kimball et al.

[11] Patent Number: 4,548,751
[45] Date of Patent: Oct. 22, 1985

[54] (2-OXO-1-AZETIDINYLOXY)-2-PROPENOIC ACID

[75] Inventors: Spencer D. Kimball, North Brunswick, N.J.; David Kronenthal, Yardley, Pa.; William H. Koster, East Amwell, N.J.

[73] Assignee: E. R. Squibb & Sons, Inc., Princeton, N.J.

[21] Appl. No.: 519,874

[22] Filed: Aug. 3, 1983

[51] Int. Cl.$^4$ .................. C07D 205/08; C07D 403/12; C07D 401/12; A61K 31/395
[52] U.S. Cl. ..................... 260/245.4; 260/239 A; 260/330.3; 260/330.9; 260/239.3 R; 544/279; 544/327; 544/335; 544/336; 544/359; 544/182; 544/215; 546/187; 546/256; 546/208; 546/275; 514/210
[58] Field of Search ............. 260/239 A, 245.4, 330.3, 260/239.3 R, 330.9; 544/279, 327, 335, 336, 359, 182, 215; 546/187, 256, 208, 275

[56] References Cited

U.S. PATENT DOCUMENTS 4,337,197 6/1982 Gordon et al. ................. 260/239 A

*Primary Examiner*—Mark L. Berch
*Attorney, Agent, or Firm*—Lawrence S. Levinson; Donald J. Barrack

[57] ABSTRACT

Antibacterial activity is exhibited by 3-acylamino-2-azetidinones having in the 1-position a group of the formula

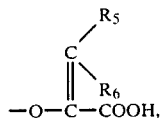

or an ester of salt thereto, wherein $R_5$ and $R_6$ are the same or different and each is hydrogen, alkyl, phenyl or substituted phenyl.

9 Claims, No Drawings

(2-OXO-1-AZETIDINYLOXY)-2-PROPENOIC ACID

RELATED APPLICATION

U.S. patent application Ser. No. 515,727, filed July 21, 1983, discloses β-lactam antibiotics and intermediates having the formula

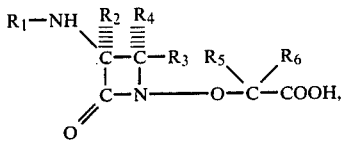

and salts and esters thereof, wherein $R_1$, $R_2$, $R_3$, $R_4$, $R_5$ and $R_6$ are as defined hereinafter.

BRIEF DESCRIPTION OF THE INVENTION

Compounds having the formula

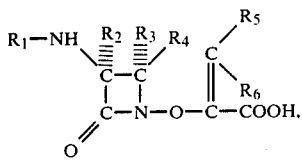

and esters and salts thereof, have antibacterial activity. In formula I, and throughout the specification, the symbols are as defined below.

$R_1$ is an acyl group derived from a carboxylic acid;

$R_2$ is hydrogen or methoxy;

$R_3$ and $R_4$ are the same or different and each is hydrogen, alkyl, alkenyl, alkynyl, cycloalkyl, phenyl, substituted phenyl or a 4, 5, 6 or 7-membered heterocycle (referred to hereinafter as $R_x$) or one of $R_3$ and $R_4$ is hydrogen and the other is azido, halomethyl, dihalomethyl, trihalomethyl, alkoxycarbonyl, 2-phenylethenyl, 2-phenylethynyl, carboxyl, —CH$_2$X$_1$ [wherein X$_1$ is azido, amino (—NH$_2$), hydroxy, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

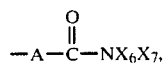

—S—X$_2$, or —O—X$_2$ (wherein A, X$_2$, X$_6$ and X$_7$ are as hereinafter defined)[, —S—X$_2$ or —O—X$_2$ [wherein X$_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl],

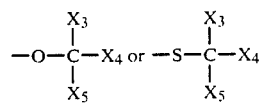

[wherein one of X$_3$ and X$_4$ is hydrogen and the other is hydrogen or alkyl, or X$_3$ and X$_4$ when taken together with the carbon atom to which they are attached form a cycloalkyl group; and X$_5$ is formyl, alkanoyl, phenylcarbonyl, (substituted phenyl)carbonyl, phenylalkylcarbonyl), (substituted phenyl)alkyl-carbonyl, carboxyl, alkoxycarbonyl, aminocarbonyl

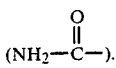

(substituted amino)-carbonyl, or cyano (—C≡N)], or

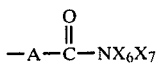

(wherein A is —CH=CH—, —(CH$_2$)$_n$—, —CH$_2$—O—, —CH$_2$—NH—, or —CH$_2$—S—CH$_2$—, n is 0, 1 or 2, and X$_6$ and X$_7$ are the same or different and each is hydrogen, alkyl, phenyl or substituted phenyl, or X$_6$ is hydrogen and X$_7$ is amino, substituted amino, acylamino or alkoxy, or X$_6$ and X$_7$ when taken together with the nitrogen atom to which they are attached form a 4, 5, 6 or 7-membered heterocycle); and $R_5$ and $R_6$ are the same or different and each is hydrogen, alkyl, phenyl or substituted phenyl.

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to cycloalkyl and cycloalkenyl groups having 3,4,5,6 or 7 carbon atoms.

The term "substituted alkyl" refers to alkyl groups substituted with one, or more, azido, amino (—NH$_2$), halogen, hydroxy, carboxy, cyano, alkoxycarbonyl, aminocarbonyl, alkanoyloxy, alkoxy, phenyloxy, (substituted phenyl)oxy, $R_x$-oxy, mercapto, alkylthio, phenylthio, (substituted phenyl)thio, alkylsulfinyl, or alkylsulfonyl groups.

The terms "alkanoyl", "alkenyl", and "alkynyl" refer to both straight and branched chain groups. These groups having 2 to 10 carbon atoms are preferred.

The terms "halogen" and "halo" refer to fluorine, chlorine, bromine and iodine.

The term "protected carboxyl" refers to a carboxyl group which has been esterified with a conventional acid protecting group. These groups are well known in the art; see, for example, U.S. Pat.No. 4,144,333, issued Mar. 13, 1979. The preferred protected carboxyl groups are benzyl, benzhydryl, t-butyl, and p-nirobenzyl esters.

The term "substituted phenyl" refers to a phenyl group substituted with 1, 2 or 3 amino (—NH$_2$), halogen, hydroxyl, trifluoromethyl, alkyl (of 1 to 4 carbon atoms), alkoxy (of 1 to 4 carbon atoms), or carboxyl groups.

The expression "a 4,5,6 or 7-membered heterocycle" (referred to as "$R_x$") refers to substituted and unsubstituted, aromatic and non-aromatic groups containing one or more nitrogen, oxygen or sulfur atoms. Exemplary substituents are oxo (=O), halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino

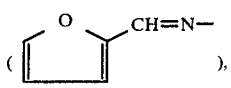

and substituted alkyl groups (wherein the alkyl group has 1 to 4 carbons). One type of "4,5,6 or 7-membered heterocycle" is the "heteroaryl" group. The term "heteroaryl" refers to those 4,5,6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetinyl, oxetanyl, thietanyl, piperidinyl, piperazinyl, imidazolidinyl, oxazolidinyl, pyrrolidinyl, tetrahydropyrimidinyl, dihydrothiazolyl and hexahydroazepinyl. Exemplary of the substituted 4,5,6 or 7-membered heterocycles are 1-alkyl-3-azetinyl, 2-oxo-1-imidazolidinyl, 3-alkylsulfonyl-2-oxo-1-imidazolidinyl, 3-benzylimino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxycarbonyl)amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-tetrahydrofuranyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having the formula $-NY_1Y_2$ wherein $Y_1$ is hydrogen, alkyl, phenyl, substituted phenyl, phenylalkyl or (substituted phenyl)alkyl, and $Y_2$ is alkyl, phenyl, substituted phenyl, phenylalkyl, (substituted phenyl)alkyl, hydroxy, cyano, alkoxy, phenylalkoxy, or amino ($-NH_2$).

The term "acyl" refers to all organic radicals derived from an organic acid (i.e., a carboxylic acid) by removal of the hydroxyl group. Certain acyl groups are, of course, preferrd but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins*, edited by Flynn, Academic Press (1972), German Offenlegungsschrift No. 2,716,677, published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, and British Pat. No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein $R_a$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

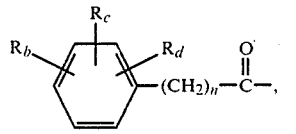

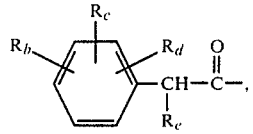

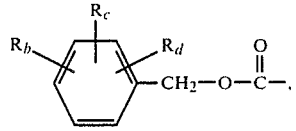

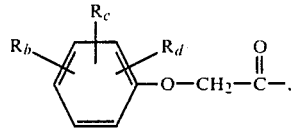

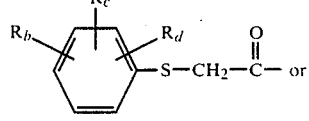

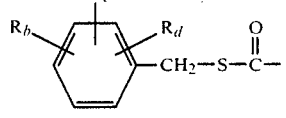

wherein n is 0, 1, 2 or 3; $R_b$, $R_c$, and $R_d$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

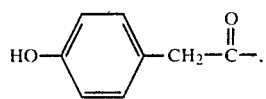

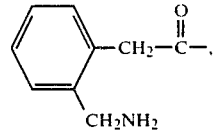

-continued

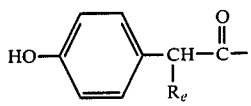

($R_e$ is preferably a carboxyl salt salt or sulfo salt) and

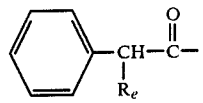

($R_e$ is preferably a carboxyl salt or sulfo salt).

(c) Heteroaromatic groups having the formula

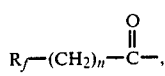

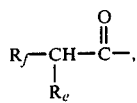

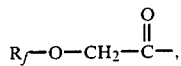

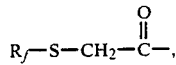

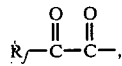

wherein n is 0, 1, 2 or 3; $R_e$ is as defined above; and $R_f$ is a substituted or unsubstituted 5-, 6- 7-membered heterocyclic ring containing 1,2,3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl, thiadiazolyl and tetrazolyl. Exemplary substituents are halogen, hydroxyl, nitro, amino, protected amino, cyano, trifluoromethyl, alkyl of 1 to 4 carbon atoms, alkoxy of 1 to 4 carbon atoms, or

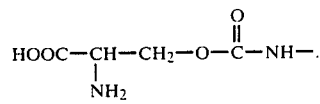

Preferred heteroaromatic acyl groups include those groups of the above formulas wherein $R_f$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)carbonyl]amino]arylacetyl groups having the formula

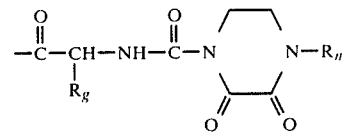

wherein $R_g$ is an aromatic group (including carbocyclic aromatics such as those of the formula

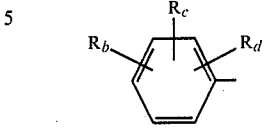

and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e., $-N=CH-R_g$ wherein $R_g$ is defined above), arylcarbonylamino (i.e.,

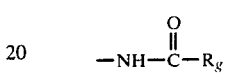

wherein $R_g$ is as defined above) or alkylcarbonylamino.

Preferred [[(4-substituted-2,3-dioxo-1-piperazinyl)carbonyl]amino]arylacetyl groups include those wherein $R_h$ is ethyl, phenylmethyleneamino or 2-furylmethyleneamino.

(e) (Substituted oxyimino)arylacetyl groups having the formula

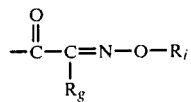

wherein $R_g$ is as defined above and $R_i$ is hydrogen, alkyl, cycloalkyl, alkylaminocarbonyl, arylaminocarbonyl (i.e.,

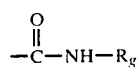

wherein $R_g$ is as defined above) or substituted alkyl (wherein the alkyl group is substituted with one or more halogen, cyano, nitro, amino mercapto, alkylthio, aromatic group (as defined by $R_g$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, or dialkoxyphosphinyl substituents).

Preferred (substituted oxyimino)arylacetyl groups include those wherein $R_g$ is 2-amino-4-thiazolyl. Also preferred are those groups wherein $R_i$ is methyl, ethyl, carboxymethyl, 1-carboxy-1-methylethyl, 2,2,2-trifluoroethyl or 1-carboxycyclopropyl.

(f) (Acylamino)arylacetyl groups having the formula

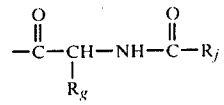

wherein $R_g$ is as defined above and $R_j$ is

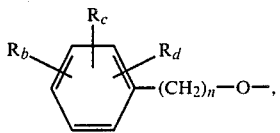

amino, alkylamino, (cyanoalkyl)amino, amido, alkylamido, (cyanoalkyl)amido,

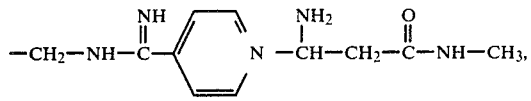

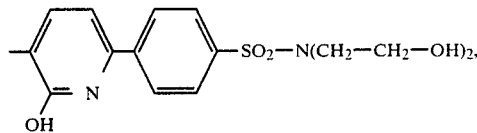

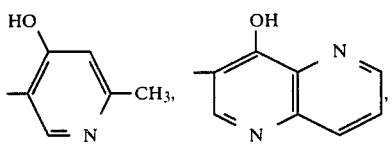

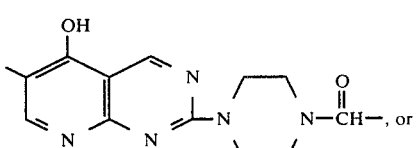

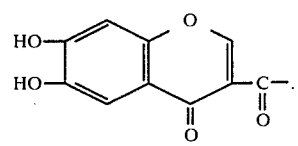

Preferred (acylamino)arylacetyl groups of the above formula include those groups wherein $R_j$ is amino or amido. Also preferred are those groups wherein $R_g$ is phenyl or 2-thienyl.

(g) [[[3-Substituted-2-oxo-1-imidazolidinyl]carbonyl]amino]arylacetyl groups having the formula

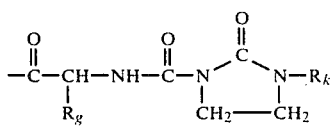

wherein $R_g$ is as defined above and $R_k$ is hydrogen, alkylsulfonyl, arylmethyleneamino (i.e., —N=CH—$R_g$ wherein $R_g$ is as defined above),

(wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups).

Preferred [[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

The terms "salt" and "salts" refer to basic salts formed with inorganic and organic bases. Such salts include ammonium salts, alkali metal salts like sodium and potassium salts (which are preferred), alkaline earth metal salts like the calcium and magnesium salts, salts with organic gases, e.g., dicyclohexylamine salt, benzathine, N-methyl-D-glucamine, hydrabamine salts, salts with amino acids like arginine, lysine and the like. The nontoxic, pharmaceutically acceptable salts are preferred, although other salts are also useful, e.g., in isolating or purifying the product.

The salts are formed in conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid and extraction with an organic solvent, e.g., ethyl acetate, dichloromethane or the like, the free acid form can be obtained, and, if desired, another salt formed.

As set forth throughout the specification. β-lactams having in the 1-position an ester of the group

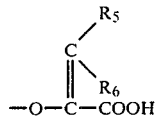

are contemplated as an integral part of this invention. Exemplary esters include alkyl, alkenyl, alkynyl, cycloalkyl, (cycloalkyl)alkyl, $R_x$-alkyl, trialkylsilylalkyl, mono-, di- or trihaloalkyl, hydroxyalkyl, alkoxyalkyl, carboxyalkyl, alkoxycarbonylalkyl, diphenylmethoxycarbonylalkyl, carbamoylalkyl, alkylcarbamoylalkyl, dialkylcarbamoylalkyl, indanyl, phenyl, substituted phenyl, phenylalkyl, (substituted phenyl)alkyl, $R_x$-carbonylalkyl,

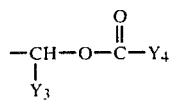

[wherein $Y_3$ is hydrogen, alkyl or phenyl and $Y_4$ is hydrogen, alkyl, cycloalkyl, (cycloalkyl)oxy, phenyl, or alkoxy, or together $Y_3$ and $Y_4$ are —(CH$_2$)$_2$—, —(CH$_2$)$_3$—, —CH=CH—, or

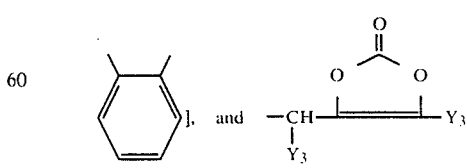

esters.

Hydrolyzable esters are those esters that can be hydrolyzed in vivo to give the parent carboxylic acid product; they exhibit the antibiotic acitivity of the parent carboxylic acid. Non-hydrolyzable esters (esters that do not hydrolze in vivo to the parent carboxylic acid) are contemplated for use in this invention as intermediates; some of them are also active as antibiotics.

β-Lactams of formula I contain at least one chiral center—the carbon atom (in the 3-position of the β-lactam nucleus) to which the acylamino substituent is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occuring cephamycins (e.g., cephamycin C).

Also included within the scope of this invention are racemic mixtures which contain the above-described β-lactams.

DETAILED DESCRIPTION OF THE INVENTION

The β-lactams of formula I, and esters and salts thereof, have activity against a range of gram-negative and gram-positive organisms. The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection ar also contemplated for use with the novel family of β-lactams of this invention. Such methods of administration include oral, intravenous, intramuscular, and as a suppository.

The β-lactams of this invention can be prepared from an amino acid having the formula

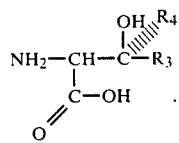

The amino group is first protected with a classical protecting group (e.g., t-butoxycarbonyl, benzyloxycarbonyl, o-nitrophenylsulfenyl, etc.), yielding the compound having the formula

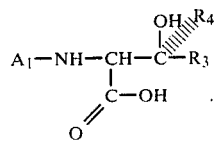

In formula III, and throughout the specification, the symbol "$A_1$" refers to a nitrogen protecting group. For certain products of formula I, the desired acyl group "$R_1$" can be used as the protecting group "$A_1$" and thus incorporated at the beginning of the reaction sequence.

The carboxyl group of a protected amino acid of formula III is then reacted with an amine having the formula

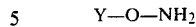

In formula IV, and throughout the specification, the symbol "Y" refers to benzyl, pivaloyl, —CH$_2$CH(NHA$_2$)CO$_2$alkyl, t-butyl, p-nitrobenzyl, benzyhydryl, 2-cyanoethyl, 2-trimethylsilylethyl, trichloroethyl, trityl, inter alia (wherein the symbol "$A_2$" refers to a nitrogen protecting group). The reaction proceeds in the presence of a coupling agent such as 1-ethyl-3-(3-dimethylaminopropyl)carbodiimide or dicyclohexylcarbodiimide, and yields a compound having the formula

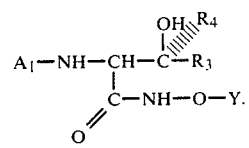

The hydroxyl group of a compound of formula V is converted to a leaving group, using, for example, a classical reagent such as methanesulfonyl chloride (methanesulfonyl is referred to hereinafter as "Ms").

The fully protected compound having the formula

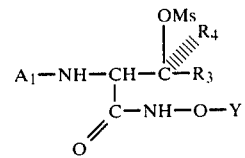

is cyclized by treatment with base, e.g., potassium carbonate. The reaction is preferably carried out in an organic solvent such as acetone, under reflux conditions, and yields a compound having the formula

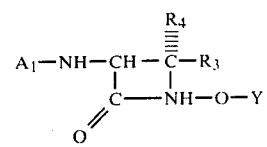

Compounds of formula VII wherein Y is benzyl are disclosed in the literature; see, for example, J.A.C.S., 104:6054 (1982).

Alternatively, cyclization of a compound of formula V can be accomplished without first converting the hydroxyl group to a leaving group. Treatment of a compound of formula V with triphenylphosphine and diethylazodicarboxylate or carbon tetrachloride, yields a compound of formula VII.

Both of the methods disclosed above for ring closure of a compound of formula V result in the inversion of the stereochemistry of the carbon atom to which the R$_3$ and R$_4$ substituents are attached.

Selective reduction of a compound of formula VII (using catalytic hydrogenation if Y is benzyl or by treatment with a base such as sodium sulfide or sodium hydroxide if Y is pivaloyl or with DBU if Y is —CH$_2$CH(NHA$_2$)CO$_2$alkyl or by treatment with acid if Y is trityl yields the corresponding compound having the formula

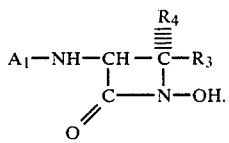

VIII

Alkylation of a hydroxamic acid of formula VIII with a bromo ester having the formula

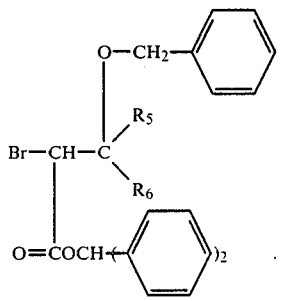

IX preferably in a solvent such as dimethylformamide in the presence of a base such as potassium carbonate yields a mixture of diastereomers having the formula

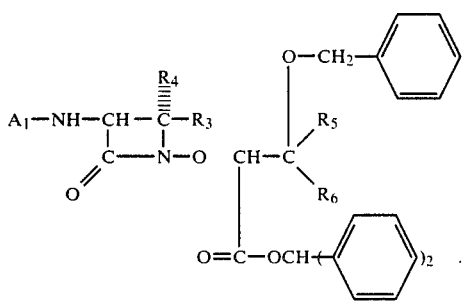

X

Catalytic hydrogenolysis of a compound of formula X removes both the benzyl and benzhydryl protecting groups to yield the corresponding compound having the formula

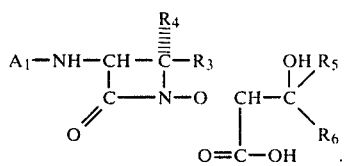

XI

Treatment of a compound of formula XI with diphenyldiazomethane yields the corresponding β-hydroxy ester having the formula

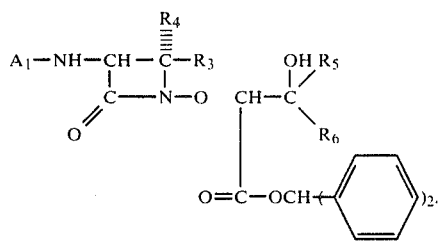

XI

A compound of formula XI can be treated with methanesulfonyl chloride in the presence of excess triethylamine to yield the elimination product having the formula

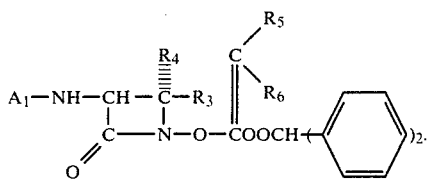

XII

Deprotection of the 3-amino substituent of a compound of formula XII can be accomplished using art-recognized techniques. If, for example, the protecting group is t-butoxycarbonyl, trifluoroacetic acid can be used to deprotect the amino group. If the protecting group is o-nitrophenylsulfenyl, p-toluenesulfonic acid can be used in combination with p-thiocresol. If acid conditions are used to deprotect the 3-amino substituent, the ester protecting group will also be removed to yield a compound having the formula

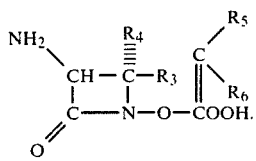

XIII

Compounds of formula XIII are key intermediates for preparing the products of formula I, and as such, form an integral part of this invention.

Well known acylation techniques can be used to acylate the 3-amino substituent of an intermediate of formula XIII to yield a product having the formula

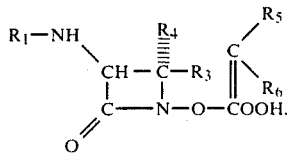

XIV

Exemplary techniques include reaction with a carboxylic acid ($R_1$—OH) or corresponding carboxylic acid halide or carboxylic acid anhydride. The reactions with a carboxylic acid proceed most readily in the presence of a carbodiimide such as dicyclohexylcarbodiimide and a substance capable of forming a reactive intermediate in situ such as N-hydroxybenzotriazole or N-hydroxysuccinimide. Alternatively, the reaction with a carboxylic acid can be run in the presence of N-methyl-N-(trimethylsilyl)trifluoroacetamide (MSTFA) and a substance capable of forming a reactive intermediate in situ such as N-hydroxybenzotriazole. In those instances wherein the acyl group ($R_1$) contains reactive functionality (such as amino or carboxyl groups) it may be necessary to first protect these functional groups, then carry out the acylation reaction, and finally deprotect the resulting product.

The products of formula I wherein $R_2$ is methoxy can be prepared from the corresponding compound of formula VII. Halogenating (preferably chlorinating) the amide nitrogen of a compound of formula VII yields a compound having the formula

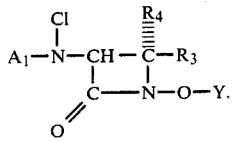

XV

Reagents and procedures of N-chlorinating amides are well known in the art. Exemplary reagents are tert.-butyl hypochlorite, sodium hypochlorite, and chlorine. The reaction can be run in an organic solvent (e.g., a lower alkanol such as methanol) or in a two phase solvent system (e.g., water/methylene chloride) in the presence of a base such as sodium borate decahydrate. The reaction is preferably run at a reduced temperature.

Reaction of a compound of formula XV with a methoxylating agent, e.g., an alkali metal methoxide, yields a compound (in combination with its enantiomer if $R_3$ and $R_4$ are the same or if XV is a racemic mixture) having the formula

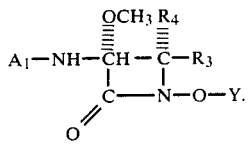

XVI

The reaction can be run in an organic solvent, e.g., a polar organic solvent such as tetrahydrofuran, at a reduced temperature.

Alternatively, a compound of formula VII can be converted to a compound of formula XVI using a single step procedure. The alkali metal methoxide can first be mixed with a compound of formula VII and the N-chlorinating reagent then added to the reaction mixture.

Conversion of a compound of formula XVI to the desired product of formula I can be accomplished using the procedures described above for the conversion of an intermediate of formula VII to a product of this invention.

The esters of products of formula I can be obtained from the corresponding carboxylic acid product using art-recognized techniques.

Bromo esters of formula IX can be obtained by bromination of an O-benzyl protected amino acid with a sodium nitrate-sodium bromide-sulfuric-acid mixture, followed by esterification with diphenyldiazomethane.

The following examples are specific embodiments of this invention.

EXAMPLE 1

[3S-[3α(Z), 4β]]-2-[[3-[[(2-Amino-4-thiazolyl)(methoxyimino)acetyl]amino]-4-methyl-2-oxo-1-azetidinyl]oxy]-2-propenoic acid, potassium salt (A) (S)-2-Bromo-3-(phenylmethoxy)propanoic acid A solution of O-(phenylmethyl)-L-serine (21.6 g, 0.108 mol) in aqueous sulfuric acid (786 ml, 2.5N) containing sodium bromide (69.3 g, 6.0 eq) was cooled to 0° C. in an ice bath. Sodium nitrite (21 g, 2.7 eq) was added over 10 minutes, and the solution stirred at 0° C. for one hour. The cooling bath was removed, ether (250 ml) was added, and stirring was continued overnight at room temperature. The aqueous layer was extracted repetitively with ether (3×100 ml), and the combined extracts were dried over anhydrous magnesium sulfate and evaporated under reduced pressure to give 25 g of a crude product. The product was purified by column chromatography (83:17; petroleum ether:ethyl acetate) to yield the title compound (10.6 g).

(B) (S)-2-Bromo-3-(phenylmethoxy)propanoic acid, diphenylmethyl ester

To a solution of (S)-2-bromo-3-(phenylmethoxy)-propanoic acid (7.63 g, 29.4 mmol) in acetone (30 ml) was added solid diphenyldiazomethane (5.81 g, 29.9 mmol) over the course of three minutes. The solution heated and nitrogen evolved vigorously. The purple solution was stirred for an additional 45 minutes, followed by the addition of acetic acid (1 ml) to quench any residual diphenyldiazomethane. The solution was extracted with saturated sodium bicarbonate (50 ml), washed with saturated sodium chloride (50 ml), dried over magnesium sulfate and evaporated at reduced pressure to give the crude product (11.24 g). Purification by chromatography on silica gel (95:5; hexane:ethyl acetate) afforded the title compound (6.38 g).

(C) (3S-trans)-2-[[3-[[(1,1-Dimethylethoxy)carbonyl]amino]-4-methyl-2-oxo-1-azetidinyl]oxy]-3-(phenylmethoxy)propanoic acid, diphenylmethyl ester To a solution of (3S-trans)-[[(1,1-dimethylethoxy)carbonyl]amino]-4-methyl-1-hydroxy-2azetidinone (55 mg, 0.26 mmol) and (S)-2-bromo-3-(phenylmethoxy)-propanoic acid, diphenylmethyl ester (110 mg, 0.26 mmol) in dimethylformamide (1 ml) was added potassium carbonate (100 mg, 1 mmol). The resulting slurry was stirred for three hours at room temperature, quenched with hydrochloric acid (1N, 10 ml) and extracted with ether (20 ml). The organic layer was washed twice with dilute hydrochloric acid (1N, 2×10 ml), with saturated sodium chloride solution (20 ml), dried over magnesium sulfate and evaporated at reduced pressure. Purification of the product by preparative thin layer chromatography afforded the title compound (108 mg) as a mixture of diastereomers.

Repetition of this reaction on a large scale (4.0 g of (S)-2-bromo-3-(phenylmethoxy)propanoic acid, diphenylmethyl ester and 2.6 g of (3S-trans)[[(1,1-dimethylethoxy)carbonyl]amino]-4-methyl-1-hydroxy-2-azetidinone) gave a quantitative yield of the same diastereomeric mixture which was used directly in the next step.

(D) (3S-trans)-2-[[3-[[(1,1-Dimethylethoxy)carbonyl]amino]-4-methyl-2-oxo-1-azetidinyl]oxy]-3-hydroxypropanoic acid (3S-trans)-2-[[3-[[(1,1-Dimethylethoxy)carbonyl]amino]-4-methyl-2-oxo-1-azetidinyl]oxy]-3-(phenylmethoxy)propanoic acid, diphenylmethyl ester was dissolved in methanol (50 ml) under nitrogen, and 10% palladium on charcoal (3.5 g) was added. Hydrogenation was carried out at room temperature and pressure for 24 hours, after which the reaction mixture was filtered through Celite. Ether (150 ml) was added and the organic phase extracted with saturated sodium bicarbonate solution (300 ml). The bicarbonate layer was separated and acidified to pH 1.8 with hydrochloric acid (6N), extracted with ethyl acetate (2×100 ml), and dried over anhydrous magnesium sulfate. Evaporation at reduced pressure gave the crude product as a hygroscopic white powder (2.09 g); it can be seen to be a

15 mixture of diastereomers by thin layer chromatography (ethyl acetate:methanol; 90:10).

(E) (3S-trans)-2-[[3-[[(1,1-Dimethylethoxy)carbonyl]amino]-4-methyl-2-oxo-1-azetidinyl]oxy], diphenylmethyl ester (3S-trans)-2-[[3-[[(1,1-Dimethylethoxy)carbonyl]amino]-4-methyl-2-oxo-1-azetidinyl]oxy]-3-hydroxypropanoic acid (1.67 g, 5.5 mmol) was dissolved in acetone (10 ml) and diphenyldiazomethane (1.16 g, 1.1 eg) was added as a solid. The reddish solution was stirred for ten minutes with the vigorous evolution of nitrogen, followed by addition of acetic acid (1 ml). Ether (75 ml) was added, and the solution extracted with saturated sodium bicarbonate (2×75 ml), washed with saturated sodium chloride (75 ml) and dried over magnesium sulfate. Evaporation at reduced pressure and dry column chromatography of the residue on silica gel (ethyl acetate) afforded the title compound (1.05 g) as a mixture of diastereomers.

(F) (3S-trans)-2-[[3-[[(1,1-Dimethylethoxy)carbonyl]amino]-4-methyl-2-oxo-1-azetidinyl]oxy]-2-propenoic acid To a solution of (3S-trans)-2-[[3-[[(1,1-dimethylethoxy)carbonyl]amino]-4-methyl-2-oxo-1-azetidinyl]oxy], diphenylmethyl ester (0.66 g, 1.4 mmol) in methylene chloride (7 ml) at −10° C. was added methanesulfonyl chloride (0.20 ml, 2.92 mmol) followed by triethylamine (0.75 ml, 5.5 mmol). The resulting solution was stirred under argon at −10° C. for one hour, washed with water (50 ml), hydrochloric acid (1N 50 ml) saturated sodium chloride (50 ml), and dried over magnesium sulfate. Evaporation under reduced pressure gave the crude title compound, which was purified by chromatography on silica gel to afford 0.54 g of the title compound, melting point 127°–130° C. This compound was recrystallized from pentane/ether to give analytically pure material, melting point 133°–134° C.

(G) [3S-[3α(Z),4β]]-2-[[3-[[2-Amino-4-thiazolyl)(methoxyimino)acetyl]amino]-4-methyl-2-oxo-1-azetidinyl]oxy]-2-propenoic acid, potassium salt To (3S-trans)-2-[[3-[[(1,1-dimethylethoxy)carbonyl]amino]-4-methyl-2-oxo-1-azetidinyl]oxy]-2-propenoic acid (155 mg, 0.34 mmol) in a round bottomed flask at −10° C. was added anisole (0.50 ml) and then trifluoroacetic acid (5.0 ml). The solution was stirred for 35 minutes at −10° C., and the volatiles removed at room temperature with a vacuum pump; the solution was then lyophilized.

The activated side chain ester was formed by adding dicyclohexylcarbodiimide (79 mg) to a solution of (Z)-2-amino-α-(methoxyimino)-4-thiazoleacetic acid (73 mg, 0.36 mmol) and N-hydroxybenzotriazole (50 mg, 0.36 mmol) in dimethylformamide (2.5 ml) at 0° C. The ice bath was removed and the solution stirred at room temperature for thirty minutes. The solution was again cooled to 0° C., and the crude trifluoroacetic acid salt above was added in dimethylformamide (1.25 ml) followed by a rinse with dimethylformamide (1.25 ml). After the addition of triethylamine (0.10 ml, 2 eq) the cooling bath was removed and the reaction mixture was stirred overnight.

Dimethylformamide was removed by evaporation under reduced pressure (room temperature) and the crude product was passed through a Dowex K+ column (12″×25 mm).

After combination of the appropriate fractions and removal of water, 220 mg of crude product was obtained. This material was chromatographed on HP-20 resin eluting with water, then with 10% acetone/water, to afford the title compound as a hygroscopic solid (7 mg), melting point 170° C. (dec). In addition to the pure material, there was obtained an additional 45 mg of material containing approximately half of the desired compound.

What is claimed is:
1. A compound having the formula

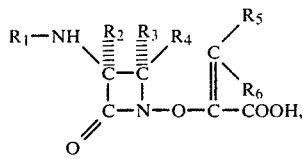

or a pharmaceutically acceptable salt or ester thereof, wherein
$R_1$ is an acyl group derived from a carboxylic acid;
$R_2$ is hydrogen or methoxy;
$R_3$ and $R_4$ are the same or different and each is hydrogen, alkyl, alkenyl, alkynyl, cycloalkyl, phenyl, substituted phenyl or a 4, 5, 6 or 7-membered heterocycle, or one of $R_3$ and $R_4$ is hydrogen and the other is azido, halomethyl, dihalomethyl, trihalomethyl, alkoxycarbonyl, 2-phenylethenyl, 2-phenylethynyl, —CH$_2$X$_1$, carboxyl, —S—X$_2$, —O—X$_2$,

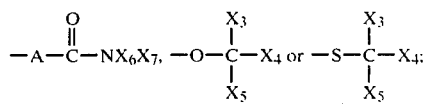

wherein $X_1$ is azido, amino, hydroxy, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

—S—X$_2$ or —O—X$_2$; X$_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroaryl carbonyl; one of $X_3$ and $X_4$ is hydrogen and the other is hydrogen or alkyl, or $X_3$ and $X_4$, when taken together with the carbon atom to which they are attached form a cycloalkyl group; $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano; A is —CH═CH—, —(CH$_2$)$_n$—, —CH$_2$—O—, —CH$_2$—NH— or —CH$_2$—S—CH$_2$; n is 0, 1 or 2; and X$_6$ and X$_7$ are the same or different and each is hydrogen, alkyl, phenyl or substituted phenyl, or X₆ is hydrogen and X₇ is amino, substituted amino, acylamino or alkoxy, or X₆ and X₇ when taken together with the nitrogen atom to which they are attached form a 4, 5, 6 or 7-membered heterocycle; and R₅ and R₆ are the same or different and each is hydrogen, alkyl, phenyl or substituted phenyl; wherein the terms "alkyl" and "alkoxy" refer to groups having 1 to 10 carbon atoms;

the term "cycloalkyl" refers to cycloalkyl groups having 3, 4, 5, 6 or 7 carbon atoms;

the term "substituted alkyl" refers to alkyl groups substituted with one, or more, azido, amino, halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl, or alkylsulfonyl groups;

the terms "alkanoyl", "alkenyl" and "alkynyl" refer to groups having 2 to 10 carbon atoms;

the term "substituted phenyl" refers to a phenyl group substituted with 1, 2 or 3 amino, halogen, hydroxyl, trifluoromethyl, alkyl (of 1 to 4 carbon atoms), alkoxy (of 1 to 4 carbon atoms) or carboxyl groups;

the term "substituted amino" refers to a group having the formula NY₁Y₂ wherein Y₁ is hydrogen, alkyl, phenyl, substituted phenyl, phenylalkyl or (substituted phenyl)alkyl, and Y₂ is alkyl, phenyl, substituted phenyl, phenylalkyl, (substituted phenyl)alkyl, hydroxy, cyano, alkoxy, phenylalkoxy or amino;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl or one of the above groups substituted with one or more halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino or substituted alkyl, wherein the alkyl group has 1 to 4 carbon atoms, groups;

the term "a 4, 5, 6 or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazoyl, triazinyl, tetrazolyl, azetinyl, oxetanyl, thietanyl, piperidinyl, piperazinyl, imidazolidinyl, oxazolidinyl, pyrrolidinyl, tetrahydropyrimidinyl, dihydrothiazolyl, hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino or substituted alkyl, wherein the alkyl group has 1 to 4 carbon atoms, groups.

2. A compound in accordance with claim 1 wherein R₂ is hydrogen.

3. A compound in accordance with claim 2 wherein R₃, R₄, R₅ and R₆ are each independently hydrogen or alkyl.

4. A compound in accordance with claim 2 wherein R₃, R₄, R₅ and R₆ are each independently hydrogen or methyl.

5. A compound in accordance with claim 2 wherein R₁ is

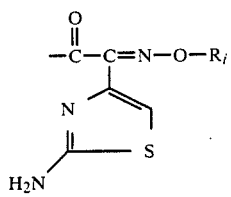

and R_i is methyl, ethyl, carboxymethyl, 1-carboxy-1-methylethyl, 2,2,2-trifluoroethyl or 1-carboxycyclopropyl.

6. A compound in accordance with claim 2 wherein R₁ is

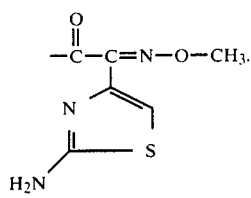

7. A compound in accordance with claim 2 wherein R₁ is

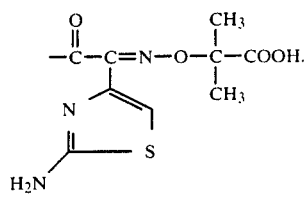

8. A compound in accordance with claim 1, [3S-[3α(Z),4β]]-2-[[3-[[(2-amino-4-thiazolyl)(methoxyimino)acetyl]amino]-4-methyl-2-oxo-1-azetidinyl]oxy]-2-propenoic acid, or a pharmaceutically acceptable salt or ester thereof.

9. A compound having the formula

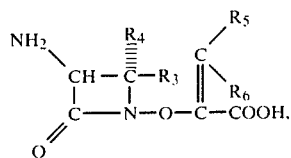

or a salt thereof, wherein

R₃ and R₄ are the same or different and each is hydrogen, alkyl, alkenyl, alkynyl, cycloalkyl, phenyl, substituted phenyl or a 4, 5, 6 or 7-membered heterocycle, or one of R₃ and R₄ is hydrogen and the other is azido, halomethyl, dihalomethyl, trihalomethyl, alkoxycarbonyl, 2-phenylethenyl, 2-phenylethynyl, —CH₂X₁, carboxyl, —S—X₂, —O—X₂,

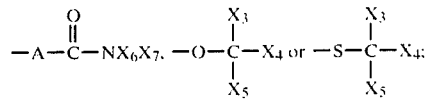

wherein X₁ is azido, amino, hydroxy, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

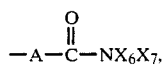

—S—$X_2$ or —O—$X_2$; $X_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl; one of $X_3$ and $X_4$ is hydrogen and the other is hydrogen or alkyl, or $X_3$ and $X_4$ when taken together with the carbon atom to which they are attached form a cycloalkyl group; $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano; A is —CH=CH—, —$(CH_2)_n$—, —$CH_2$—O—, —$CH_2$—NH— or —$CH_2$—S—$CH_2$; n is 0, 1 or 2; and $X_6$ and $X_7$ are the same or different and each is hydrogen, alkyl, phenyl or substituted phenyl, or $X_6$ is hydrogen and $X_7$ is amino, substituted amino, acylamino or alkoxy, or $X_6$ and $X_7$ when taken together with the nitrogen atom to which they are attached form a 4, 5, 6 or 7-membered heterocycle; and $R_5$ and $R_6$ are the same or different and each is hydrogen, alkyl, phenyl or substituted phenyl;

wherein the terms "alkyl" and "alkoxy" refer to groups having 1 to 10 carbon atoms;

the term "cycloalkyl" refers to cycloalkyl groups having 3, 4, 5, 6 or 7 carbon atoms;

the term "substituted alkyl" refers to alkyl groups substituted with one, or more, azido, amino, halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl, or alkylsulfonyl groups;

the terms "alkanoyl", "alkenyl" and "alkynyl" refer to groups having 2 to 10 carbon atoms;

the term "substituted phenyl" refers to a phenyl group substituted with 1, 2 or 3 amino, halogen, hydroxyl, trifluoromethyl, alkyl (of 1 to 4 carbon atoms), alkoxy (of 1 to 4 carbon atoms) or carboxyl groups;

the term "substituted amino" refers to a group having the formula $NY_1Y_2$ wherein $Y_1$ is hydrogen, alkyl, phenyl, substituted phenyl, phenylalkyl or (substituted phenyl)alkyl, and $Y_2$ is alkyl, phenyl, substituted phenyl, phenylalkyl, (substituted phenyl)alkyl, hydroxy, cyano, alkoxy, phenylalkoxy or amino;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl or, one of the above groups substituted with one or more halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino or substituted alkyl, wherein the alkyl group has 1 to 4 carbon atoms, groups;

the term "a 4, 5, 6 or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazoyl, triazinyl, tetrazolyl, azetinyl, oxetanyl, thietanyl, piperidinyl, piperazinyl, imidazolidinyl, oxazolidinyl, pyrrolidinyl, tetrahydropyrimidinyl, dihydrothiazolyl, hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, or substituted alkyl; wherein the alkyl group has 1 to 4 carbon atoms, groups.

* * * * *

UNITED STATES PATENT AND TRADEMARK OFFICE
CERTIFICATE OF CORRECTION

PATENT NO. : 4,548,751  Page 1 of 2
DATED    : October 22, 1985
INVENTOR(S) : Spencer D. Kimball et al.

It is certified that error appears in the above—identified patent and that said Letters Patent is hereby corrected as shown below:

Please correct formula X to read as follows:

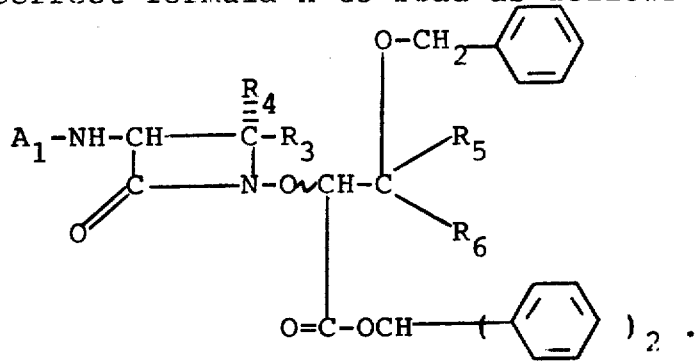

Please correct formula XI to read as follows:

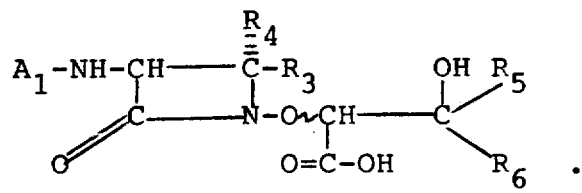

UNITED STATES PATENT AND TRADEMARK OFFICE
CERTIFICATE OF CORRECTION

PATENT NO. : 4,548,751

DATED : October 22, 1985

INVENTOR(S) : Spencer D. Kimball et al.

It is certified that error appears in the above—identified patent and that said Letters Patent is hereby corrected as shown below:

Please correct the second formula XI to read as follows:

XIa
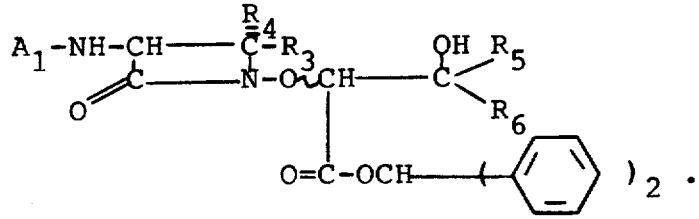

Column 12, line 1, please delete "XI" and replace it with --XIa--.

Signed and Sealed this

Fourteenth Day of January 1986

[SEAL]

Attest:

DONALD J. QUIGG

Attesting Officer

Commissioner of Patents and Trademarks